(12) United States Patent
Hutchins

(10) Patent No.: US 8,110,563 B1
(45) Date of Patent: Feb. 7, 2012

(54) FIRE ANT KILLER ("F.A.K.")/ INSECTICIDE

(76) Inventor: Harold V. Hutchins, Ninety Six, SC (US)

( * ) Notice: Subject to any disclaimer, the term of this patent is extended or adjusted under 35 U.S.C. 154(b) by 158 days.

(21) Appl. No.: 12/471,373

(22) Filed: May 23, 2009

Related U.S. Application Data

(60) Provisional application No. 61/055,639, filed on May 23, 2008.

(51) Int. Cl.
- *A01N 33/26* (2006.01)
- *A01N 37/22* (2006.01)
- *A61K 31/21* (2006.01)

(52) U.S. Cl. ......... 514/150; 514/506; 514/520; 514/526

(58) Field of Classification Search .................. None
See application file for complete search history.

(56) References Cited

U.S. PATENT DOCUMENTS

| | | |
|---|---|---|
| 3,575,349 A | 4/1971 | Stahl et al. |
| 3,782,026 A | 1/1974 | Bridges et al. |
| 4,160,336 A | 7/1979 | Query |
| 4,756,118 A | 7/1988 | Evans, II |
| 4,768,306 A | 9/1988 | Hillbun |
| 4,815,234 A | 3/1989 | Connolly |
| 4,817,329 A | 4/1989 | Forbes |
| 4,829,706 A | 5/1989 | Perry |
| 4,891,222 A | 1/1990 | Eichhoefer |
| 5,031,355 A | 7/1991 | Ryan |
| 5,054,231 A | 10/1991 | Witherspoon |
| 5,109,629 A | 5/1992 | King, Jr. et al. |
| 5,154,018 A | 10/1992 | Livingston |
| 5,198,467 A | 3/1993 | Milks |
| 5,319,878 A | 6/1994 | Moffett et al. |
| 5,325,626 A | 7/1994 | Jackson |
| 5,501,032 A | 3/1996 | Pitman |
| 5,561,942 A | 10/1996 | Mugno et al. |
| 5,679,365 A | 10/1997 | Henderson et al. |
| 5,700,039 A | 12/1997 | Manning |
| 5,870,852 A | 2/1999 | Stanley |
| 5,881,493 A | 3/1999 | Restive |
| 5,946,851 A | 9/1999 | Adey et al. |
| 6,026,609 A | 2/2000 | Rawls |
| 6,079,149 A | 6/2000 | Hastings |
| 6,308,454 B1 | 10/2001 | Powell |
| 6,604,318 B1 | 8/2003 | Cassidy |
| 6,609,330 B1 | 8/2003 | Heitman |
| 6,797,490 B2 | 9/2004 | Bulla et al. |
| 6,908,052 B1 | 6/2005 | Jacobson |
| 6,966,143 B2 | 11/2005 | Allen |
| 7,363,746 B2 | 4/2008 | Spies et al. |
| 2003/0131523 A1 | 7/2003 | Rawls |
| 2005/0155278 A1 | 7/2005 | Rawls |
| 2006/0073180 A1 | 4/2006 | Steward |
| 2007/0056209 A1 | 3/2007 | Schuster |
| 2007/0137095 A1 | 6/2007 | Chen |
| 2008/0070787 A1* | 3/2008 | Pullen .................. 504/362 |
| 2009/0208546 A1* | 8/2009 | Shirley et al. .......... 424/405 |

* cited by examiner

*Primary Examiner* — Alton Pryor

(57) ABSTRACT

The present invention features a composition for killing fire ants. In some embodiments, the composition comprises an insecticide and a triclosan composition. In some embodiments, the composition is a liquid composition.

4 Claims, No Drawings

FIRE ANT KILLER ("F.A.K.")/ INSECTICIDE

CROSS REFERENCE

The present non-provisional patent application claims benefit to the earlier priority date of provisional patent application Ser. No. 61/055,639, the disclosure of which is incorporated in its entirety herein by reference.

BACKGROUND OF THE INVENTION

FAK is a liquid composition created for the eradication of fire ants and their mound. FAK destroys on contact as opposed to the granular mixes requires time to activate. FAK is an environmentally friendly insecticide that can be used in multiple scenarios ranging from spot spraying the mounds in any location around the home or businesses to spraying inside the home or businesses. When properly prepared, FAK kills the first few fire ants and saturates deep into the colony or mound to kill the eggs queen in minutes and is immediately safe for activities by pets or children.

DESCRIPTION OF PREFERRED EMBODIMENTS

The present invention features a composition for killing fire ants. In some embodiments, the composition comprises an insecticide and a triclosan composition. In some embodiments, the composition is a liquid composition.

In some embodiments, the insecticide comprises a lambda cyhalothrin. Lambda-cyhalothrin is a pyrethroid insecticide. Two brand names are Triazide and Hot Shot.

In some embodiments, the triclosan composition comprises about 0.1% to about 1.0% triclosan. Triclosan (IUPAC name is 5-chloro-2-(2,4-dichlorophenoxy)phenol)) is found in soaps and detergent at about 0.10-1.00%. Triclosan is also found in deodorants, toothpastes, shaving creams, mouth washes, and cleaning supplies and is infused in an increasing number of consumer products, such as kitchen utensils, toys, bedding, socks, and trash bags. Triclosan has been shown to be effective in reducing and controlling bacterial contamination on the hands and on treated products. More recently, showering or bathing with 2% triclosan has become a recommended regimen for the decolonization of patients whose skin is carrying methicillin resistant *Staphylococcus aureus* (MRSA) following the successful control of MRSA outbreaks in several clinical settings. Triclosan is regulated by both the U.S. Food and Drug Administration, the Environmental Protection Agency, and the European Union. Detergent products known to have triclosan includes Dawn, Joy, Palmolive and Equate dish detergents.

In some embodiments, the composition further comprises one or more of the following ingredients: sodium lauryl sulfate, sodium laureth sulfate, C12-14-16 dimethyl amine oxide, SD alcohol, sodium chloride, PPG-26, PEI-14 PEG-10/PPG-7 copolymer, cyclohexanediamine, phenoxyethanol, magnesium chloride, methylisothlazolinone, fragrance, yellow 5, blue 1.

In some embodiments, the triclosan composition comprises one or more of the following ingredients: sodium lauryl sulfate, sodium laureth sulfate, C12-14-16 dimethyl amine oxide, SD alcohol, sodium chloride, PPG-26, PEI-14 PEG-10/PPG-7 copolymer, cyclohexanediamine, phenoxyethanol, magnesium chloride, methylisothlazolinone, fragrance, yellow 5, blue 1.

In some embodiments, the insecticide is at about 0.070% to about 0.100% of the composition and the triclosan composition is at about 0.050% to about 0.080% of the composition. In some embodiments, the insecticide is at about 0.080% to about 0.090% of the composition and the triclosan composition is at about 0.060% to about 0.070% of the composition. In some embodiments, the insecticide is at about 0.087% of the composition and the triclosan composition is at about 0.067% of the composition. In some embodiments, the remainder of the FAK composition comprises one or more of the following sodium lauryl sulfate, sodium laureth sulfate, C12-14-16 dimethyl amine oxide, SD alcohol, sodium chloride, PPG-26, PEI-14 PEG-10/PPG-7 copolymer, cyclohexanediamine, phenoxyethanol, magnesium chloride, methylisothlazolinone, fragrance, yellow 5, blue 1.

For use, the FAK compositions above may be diluted. For example, the composition may be diluted at about 1-3 ounces, e.g., 2 ounces, to about 0.75 to 1.25, e.g., about 1 gallon, of a solution. In some embodiments, the solution comprises water. In some embodiments, the FAK composition is diluted with water at a ratio of 2 ounces of FAK composition to 1 gallon of water.

The following protocols are non-limiting examples.

EXAMPLE 1

The FAK composition may be prepared in the following ways. Prepare 0.08% insecticide (e.g., lambda cyhalothrin), 0.040% dish detergent comprising a triclosan, and 98.8% of inactive ingredient. In some embodiments, the inactive ingredient comprises other ingredients from the insecticide source for the lambda cyhalothrin and other ingredients from the dish detergent source for the triclosan. Then dilute 2 ounce of the FAK composition in one gallon of water for use.

EXAMPLE 2

The FAK composition may be prepared in the following ways. Use 132 ounce of liquid dish detergent having a triclosan to 64 ounce of insecticide. Then dilute 2 ounce of the FAK composition in one gallon of water for use.

EXAMPLE 3

Making a FAK composition:

| | | |
|---|---|---|
| Lambda-Cyhalothrin | 0.087% | 0.0246 ml per ounce |
| Triclosan | 0.065% | 0.0184 ml per ounce |
| Inactive | 99.848 | 28.2696 ml per ounce |
| FAK Ingredients: (by product name used) Concentrate Only | | |
| Triazicide | 33.33% | 9.428 ml per ounce |
| Dawn, Joy, Palmolive, Equate Dish Detergent | 66.67% | 18.856 ml per ounce |
| Inactive ingredients: 99.848% water, sodium lauryl sulfate, sodium laureth sulfate, C12-14-16 dimethyl amine oxide, SD alcohol, sodium chloride, PPG-26, PEI-14 PEG-10/PPG-7 copolymer, cyclohexanediamine, phenoxyethanol, magnesium chloride, methylisothlazolinone, fragrance, yellow 5, blue 1. | | |

Then dilute 2 ounce of the FAK composition in one gallon of water for use.

EXAMPLE 4

The FAK composition may be used in the following ways:
(A) Perimeter spray as other insecticide are used to provide barrier protection and residue kill.

(B) Broadcast spray over large areas such as yards, animal pens, fields, gardens, and trees.

(C) Applied directly on pets as a spray or shampoo for fleas.

(D) Mixed with ornamental grass herbicides for dual application.

(E) FAK can also kill other ants, spiders, roaches, wasps, beetles and fleas. It has also been used to kill the spinning worms on pecan trees without harming other wildlife.

EXAMPLE 5

Preparation of diluted FAK composition for use: Measure 2 ounces of FAK composition per gallon of water. Pour FAK composition into sprayer already with desired amount of water in sprayer. Agitate mound without spreading ants or dirt. Immediately spray the diluted FAK composition onto the agitated mound to totally saturate the mound and 1-2 feet area around the base of the mound.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A composition for killing fire ants, the composition comprising lambda cyhalothrin and a triclosan composition wherein the lambda cyhalothrin is at about 0.080% to about 0.090% of the composition and the triclosan composition is at about 0.060% to about 0.070% of the composition.

2. The composition of claim 1 wherein the lambda cyhalothrin is at about 0.087% of the composition and the triclosan composition is at about 0.067% of the composition.

3. The composition of claim 1 being diluted with a solution to a ratio of about two ounces of the composition to about one gallon of a solution.

4. The composition of claim 2 being diluted with a solution to a ratio of about two ounces of the composition to about one gallon of a solution.

* * * * *